United States Patent [19]

Vogt et al.

[11] Patent Number: 4,529,560
[45] Date of Patent: Jul. 16, 1985

[54] PROCESS FOR MAKING ACETIC ANHYDRIDE

[75] Inventors: Wilhelm Vogt, Hürth; Erhard Jägers, Bornheim; Hermann Glaser, Erftstadt, all of Fed. Rep. of Germany

[73] Assignee: Hoechst Aktiengesellschaft, Fed. Rep. of Germany

[21] Appl. No.: 515,284

[22] Filed: Jul. 19, 1983

[30] Foreign Application Priority Data

Aug. 28, 1982 [DE] Fed. Rep. of Germany ....... 3232066

[51] Int. Cl.$^3$ ............................................. C07C 51/54
[52] U.S. Cl. ..................................... 260/546; 260/549
[58] Field of Search ............................... 260/549, 546

[56] References Cited

U.S. PATENT DOCUMENTS 4,115,444 9/1978 Rizkalla ............................... 260/549
4,140,865 2/1979 Fernholz et al. ................... 562/519

*Primary Examiner*—Natalie Trousof
*Assistant Examiner*—L. Hendriksen
*Attorney, Agent, or Firm*—Connolly and Hutz

[57] ABSTRACT

The disclosure relates to a process for making acetic anhydride by reacting methyl acetate and/or dimethylether with carbon monoxide, which may be used in admixture with up to 30 volume % hydrogen, under practically anhydrous conditions at temperatures of 390° to 540° K., under pressures of 1 to 300 bars in the presence of a catalyst system containing nickel or nickel compounds, iodine and/or its compounds as well as a tertiary or quaternary organic nitrogen, phosphorus, arsenic or antimony compound. More particularly a catalyst system is used which contains vanadium or niobium or a compound thereof as an additional constituent.

3 Claims, No Drawings

PROCESS FOR MAKING ACETIC ANHYDRIDE

The present invention relates to a process for making acetic anhydride by reacting methyl acetate and/or dimethylether with carbon monoxide, which may be used in admixture with up to 30 volume % hydrogen, under practically anhydrous conditions, at temperatures of 390 to 540 K., under a pressure of 1 to 300 bars in the pesence of a catalyst system containing nickel or nickel compounds, iodine and/or its compounds as well as a tertiary or quaternary organic nitrogen, phosphorus, arsenic or antimony compound.

Such process has already been described in U.S. Pat. No. 2,729,651. The feed materials used therein are basically selected from nickel complexes, which include e.g. triphenylethylphosphonium nickel tetriodide, but tetramethylammonium iodide and nickel iodide or nickel powder, iodine, triethylamine and ethyl iodide can, for example, also be used. Although the reaction is carried out under pressures of up to 700 bars, acetic anhydride is obtained in low space/time-yields for reaction periods between 5 and 26 hours. Needless to say this is a commercially unattractive process in view of the high pressures used and low space/time-yields obtained.

As a result of the corrosiveness of the reaction medium, it is necessary for the autoclave to be made up of an alloy of Hastelloy B or C or tantalum which naturally entails heavy investment of capital for effecting such carbonylation processes.

The present invention now provides a catalyst system containing vanadium or niobium or their compounds as an additional constituent, which unexpectedly permits the catalyst system described in U.S. Pat. No. 2,729,651 to be activated, i.e. the space/time yields to be considerably improved and the commercial attractiveness of the process to be critically improved.

The process of this invention carried out at temperatures of 460 K. permits space/time yields to be obtained which are comparable to those obtained with a considerably more expensive rhodium catalyst system. Despite the presence of hydrogen, ethylidene diacetate could not be found to form.

The useful nickel compounds comprise e.g. nickel carbonyl, nickelacetyl acetonate, nickel halides, nickel acetate, nickel sulfate or nickel cyanide.

Vanadium or niobium can be used as metal or compounds of whatever oxidation stage, e.g. as chlorides ($VCl_3$, $NbCl_5$), vanadyl(V)alkylate or acetyl acetonates ($VO(C_5H_7O_2)_2$). The molar ratio of Ni:V or Ni:Pb preferably is 1:(0.1–4).

Methyl iodide or hydrogen iodide is the iodine compound which is preferably used. The useful organonitrogen or organophosphorus compounds comprise amines, phosphines or aminophosphines, e.g. trialkylamines, N,N-dialkylaniline, pyridine, N-methylimidazole, 3-picoline, 2,4-lutidine, 3,4-lutidine, quinoline, trialkylphosphines, such as tributylphosphine, trioctylphosphine, trilaurylphosphine or triarylphosphines, such as triphenylphosphine. Organonitrogen or organophosphorus compounds quaternized with a methyl halide or hydrogen halide, e.g. N-methylpyridinium halide, N,N-dimethylimidazolium halide, N-methyl-3-picolinium halide, N-methyl-2,4-lutidinium halide, N-methyl-3,4-lutidinium halide, N-methylquinolinium halide, tributylmethylphosphonium halide, trioctylmethylphosphonium halide, trilaurylmethylphosphonium halide, triphenylmethylphosphonium halide, can also be used, the halide being chloride or bromide or preferably iodide. Arsines and stibines should preferably be used as organic arsenic and antimony compounds. Speaking generally, the organophosphorus compounds are preferred.

The individual reactants, i.e. methyl acetate or dimethylether/nickel(compound)/iodine(compound)/nitrogen, phosphorus, arsenic or antimony compound/vanadium(compound) or niobium(compound) should preferably be used in a molar ratio of 1:(0.001–0.1):(0.01–1):(0.01–1):(0.0005–0.1).

The carbonylation reaction of this invention can also be effected in the presence of solvents which should suitably be selected from acetic acid or amides, such as N-methylpyrrolidone, N,N-diethyl acetamide or sulfur-containing solvents, such as sulfolane.

The process of this invention can be carried out under pressures substantially lower than the process described in U.S. Pat. No. 2,729,651, preferably under pressures of 40 to 150 bars, which means considerably less expenditure of capital for pressure-resisting apparatus.

EXAMPLE 1

(Comparative Example)

250 g methyl acetate, 50 g methyl iodide, 102 g methyltributylphosphonium iodide and 7.66 g nickel(II)acetyl acetonate were reacted at 460 K. in a Hastelloy autoclave with 100 bars carbon monoxide. 172.6 g acetic anhydride, corresponding to a space/time-yield of 106.4 g $Ac_2O$ per liter reaction solution per hour was obtained after a reaction period of 265 minutes.

EXAMPLE 2

(Comparative Example)

250 g methyl acetate, 50 g methyl iodide, 102 g methyltributylphosphonium iodide and 7.66 g nickel(II)acetyl acetonate were reacted with 100 bars $CO/H_2$ (ratio by volume=10:1) at 460 K. 165 g acetic anhydride, corresponding to a space/time-yield of 142 g $Ac_2O$ per liter reaction solution per hour was obtained after a reaction period of 188 minutes.

EXAMPLE 3

250 g methyl acetate, 50 g methyl iodide, 102 g methyltributylphosphonium iodide, 7.66 g nickel(II)acetyl acetonate and 9.44 g vanadium(III)chloride were reacted at 460 K. with 100 bars CO. 185 g acetic anhydride, corresponding to 149 g $Ac_2O$ per liter reaction solution per hour was obtained after a reaction period of 200 minutes.

EXAMPLE 4

250 g (3.38 mols) methyl acetate, 50 g (0.352 mol) methyl iodide, 102 g (0.296 mol) methyltributylphosphonium iodide, 7.66 g (0.03 mol) nickel(II)acetyl acetonate, and 7.3 g (0.03 mol) vanadyl(V)-n-propylate ($VO(OC_3H_7)_3$) were reacted with 100 bars $CO/H_2$ (ratio by volume=10:1) at 460 K. 172 g acetic anhydride, corresponding to a space/time-yield of 515.2 g $Ac_2O$ per liter reaction solution per hour was obtained after a reaction period of 54 minutes.

EXAMPLE 5

250 g methyl acetate, 50 g methyl iodide, 102 g methyltributylphosphonium iodide, 7.66 g (0.03 mol) nickel(II)acetyl acetonate and 9.44 g (0.06 mol) vanadium- (III)chloride were reacted at 475 K. with 100 bars CO/H$_2$ (ratio by volume=10:1). 163 g acetic anhydride, corresponding to a space/time-yield of 732.4 g Ac$_2$O per liter reaction solution per hour was obtained after a reaction period of 36 minutes.

EXAMPLE 6

250 g methyl acetate, 50 g methyl iodide, 102 g methyltributylphosphonium iodide, 7.66 g (0.03 mol) nickel(II)acetyl acetonate and 16.2 g (0.06 mol) niobium(V)-chloride were reacted at 460 K. with 100 bars CO/H$_2$ (ratio by volume=10:1). 159 g acetic anhydride, corresponding to a space/time-yield of 274 g Ac$_2$O per liter reaction solution per hour was obtained after a reaction period of 94 minutes.

EXAMPLE 7

250 g methyl acetate, 50 g methyl iodide, 102 g methyltributylphosphonium iodide, 5.12 g (0.03 mol) nickel tetracarbonyl, and 7.92 g (0.03 mol) vanadyl(IV)acetyl acetonate were reacted at 460 K. with 100 bars CO/H$_2$ (ratio by volume=10:1). 179.9 g acetic anhydride, corresponding to a space/time-yield of 834 g Ac$_2$O per liter reaction solution per hour was obtained after a reaction period of 35 minutes.

We claim:

1. A process for making acetic anhydride from methyl acetate or dimethyl ether and carbon monoxide, comprising:
    reacting the methyl acetate or dimethyl ether with the carbon monoxide under substantially anhydrous conditions at temperatures of 390 to 540 K., under pressures of 1 to 300 bars in the presence of a catalyst system, said catalyst system comprising catalytic metal or metal compounds and iodine or its compound and a tertiary or quaternary organic compound selected from the group consisting of compounds of nitrogen, phosphorus, arsenic and antimony,
    said catalytic metal or metal compounds consisting essentially of nickel or nickel compounds and vanadium or niobium or a compound thereof as an additional constituent.

2. A process as claimed in claim 1, wherein methyl acetate or dimethylether/nickel(compound)/iodine(compound)/nitrogen, phosphorus, arsenic or antimony compound/vanadium(compound) or niobium(compound) are used in a molar ratio of 1:(0.001–0.1):(0.01–1):(0.01–1):(0.0005–0.1).

3. A process as claimed in claim 1, wherein the carbon monoxide is used in admixture with up to 30 volume % hydrogen.

* * * * *